April 4, 1933. A. J. AMLING ET AL Plant Pat. 59
HYBRID TEA ROSE
Filed June 21, 1932
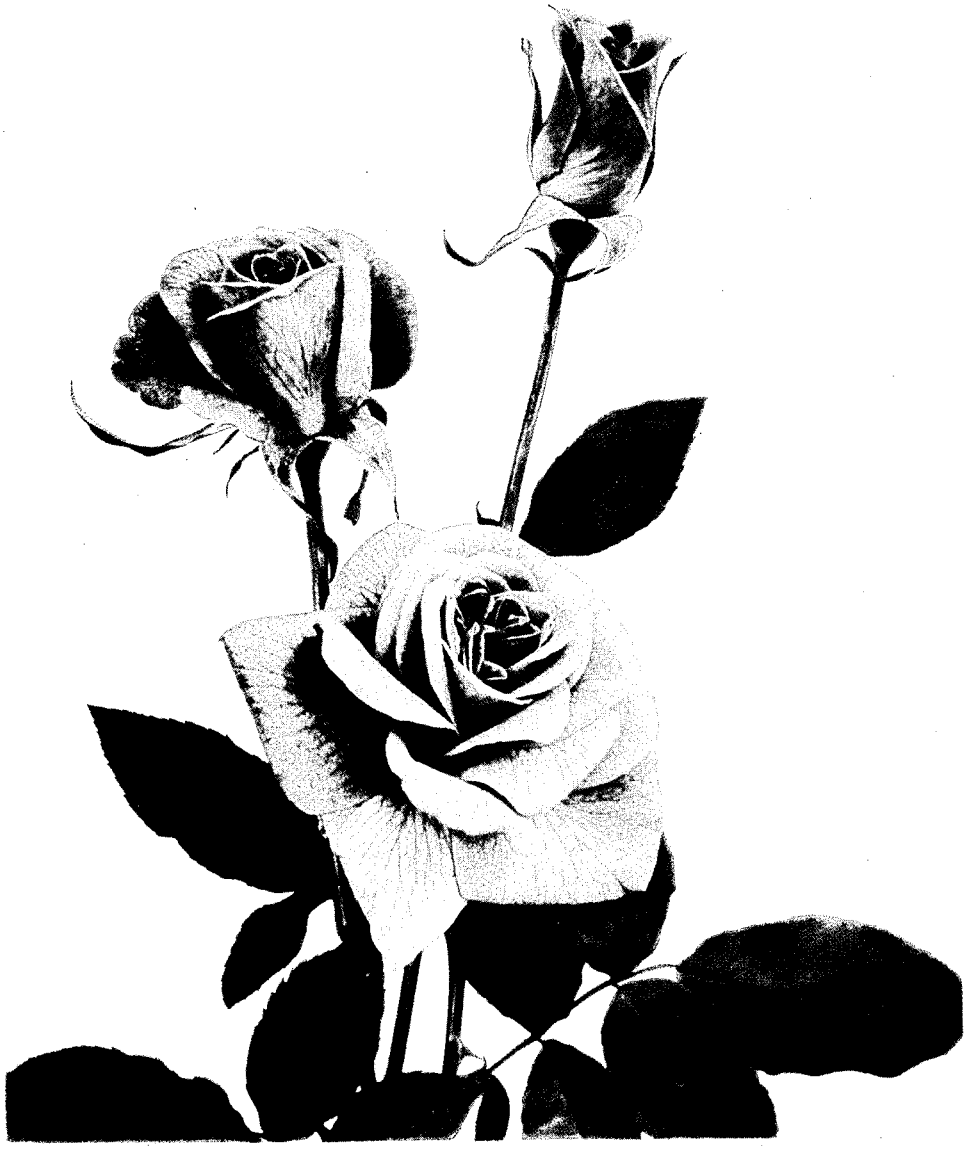
INVENTORS
Albert J. Amling
Ernst C. Amling
By Orville M Kile
PLANT PATENT AGENT Patented Apr. 4, 1933

Plant Pat. 59

UNITED STATES PATENT OFFICE

ALBERT J. AMLING AND ERNST C. AMLING, OF ORANGE, CALIFORNIA, ASSIGNORS TO AMLING BROTHERS, OF SANTA ANA, CALIFORNIA, A PARTNERSHIP

HYBRID TEA ROSE

Application filed June 21, 1932. Serial No. 618,566.

Our present invention relates to improvements in fragrant, red hybrid tea roses, the objects of our invention being, briefly stated, to provide a rose of the type mentioned having flowers of superior size, petallage, form and color, and having vigorous growing and producing habits and other desirable characteristics.

Our new rose is a sport of the variety talisman and was discovered by the first named joint inventor after search made through a large number of roses grown on the premises of Amling Brothers, and was propagated, tested and developed by the second named joint inventor. It had not at the date of application been introduced to the public.

The accompanying illustrations, in the originals, show in approximately natural size, a bud just beginning to open, a bud partly opened, and a flower two-thirds opened. The color represents the natural appearance of the blossoms on the bush or after being cut only a few hours.

The following is a detailed description of this rose plant and flower:

The bush or plant under average good greenhouse conditions grows 4 to 5 feet tall. It has the vigorous growth and prolific production qualities characteristic of the talisman variety. It is relatively free from plant diseases.

*Stems.*—Stout, light green, entirely free of spines or thorns on the first 5 to 8 inches below the blossom. No spines are found at any point on the stem of a typical specimen. The thorns are relatively few in number, pinkish, straight and set almost at right angles to the stem but pointing slightly downward.

*Foliage.*—"Forest green" color (according to Ridgeway's Color Standards and Nomenclature), not glossy, and lightly serrated. The leaf branches on the flower-bearing stems carry from 3 to 7 leaves each, the smaller number being nearer the flower. Four to six inches below the flower a single leaflet is frequently found but no leaves occur less than 4 to 5 inches below the flower on a normal or typical specimen. The second and third leaf branches below the flower usually have very large leaves, the terminal leaf generally measuring 3 to 4 inches long along the midrib and 1¾ to 2 inches across at the widest point. While the first and second leaf branches below the flower do not have thorns on the underneath side of the petiole the lower leaf branches have one to five sharp and rather large thorns.

*Stipules.*—Medium size, without foliaceous tips or appendages and having no tendency to curl.

*Hips.*—Rather wide and tapering sharply.

*Buds.*—Long, urn-shaped to pointed but readily distinguished from talisman type of bud by the absence of very long and foliaceous sepals enclosing and extending beyond the end of the bud. Buds are ordinarily 1½ to 2 inches long and 1¼ inches across the base. The tightly rolled and slightly opened buds are of approximately "carmine" color, according to Ridgeway's Color Standard and Nomenclature (Plate I). At the base of each petal and plainly noticeable is an area of yellow shading from "light cadmium" (Plate IV) to "Primuline yellow" (Plate XVI).

*Sepals.*—Normally 5 in number. Decidedly different from the typical talisman type sepals in that they are relatively wide and of only medium length rather than long and leaflike.

*Blossoms.*—Large, ordinarily measuring 4 to 5 inches across the top when fully opened. Decidedly double, having in early June in the vicinity of Chicago approximately 20 large ovate petals, approximately 25 smaller central petals of obovate to oblong shape, and a dozen or more rudimentary petals. The imbricated arrangement of the petals together with the large number of central petals gives the fully opened flower a dahlia-like appearance, the center being filled in so as to almost completely conceal the stamens and pistils. At the same time the outer whorls of petals curl back toward the stem, thereby further increasing the apparent size of the flower.

As above stated the color of the newly opening bud is approximately "carmine." As the bud opens farther the colors become lighter and when two-thirds opened the color is between "Tyrian rose" and "rose color" (Plate XII), gradually lightening into "rose color" and then taking on slightly purple tints. As the flower passes beyond its prime and begins to fade, instead of becoming bluish or dark purple as occurs in many red varieties, the color lightens and becomes approximately "Tyrian pink" to "rose pink" (Plate XII).

While this rose throughout its life retains the yellow or cadmium color at the base of the petals, on both surfaces, the large number of petals and the manner in which the flower opens prevents the yellow from being visible except occasionally a petal will turn back far enough to reveal a slight touch of this yellow color.

The inner petals to the number of 20 or more have a white strip up the middle of each from base to top but often visible only on the under surface.

The veining of the petals, which is scarcely noticeable in the opening bud becomes quite distinct as the flower ages, being much more pronounced on the upper surface than on the lower.

Both the stamens and the pistils are red or pink in color and the anthers are brown edged with yellowish centers. The tops of the pistils are light. Moderate in number rather than excessive.

The principal features which in combination readily distinguish our new variety from all other known varieties of roses ordinarily designated as red are;

*One.*—The distinctive color effects, particularly the changes from the carmine bud to the rose color and rose pink of the opened flower, together with the yellow color so noticeable on the basal area of the bud and opening flower. These features—not to mention various physical features of the foliage and the form of flower—readily distinguish this variety from the variety "Mary Hart" which has no visible yellow color either on bud or opening flower, and which does not assume a rose or pink color when opened.

*Two.*—The large number of petals in imbricated arrangement and the full center when opened.

*Three.*—The freedom from spines and thorns on the upper part of the flower stems.

*Four.*—The large size of the leaves near the blossoms and smooth rather than veined appearance of the leaves.

*Five.*—The lack of foliaceous sepals and stipules so frequently found in sports of the talisman rose.

What we claim as new is:

The variety of hybrid tea rose herein shown and described, characterized particularly by its carmine buds changing to various shades of pink in the opened flower, its full petallage and pleasing form, and its superior growing qualities.

In testimony whereof we affix our signatures.

ALBERT J. AMLING.
ERNST G. AMLING.